(12) United States Patent
Grammenos et al.

(10) Patent No.: US 6,255,352 B1
(45) Date of Patent: Jul. 3, 2001

(54) METHOD FOR COMBATING HARMFUL FUNGI

(75) Inventors: Wassilios Grammenos, Ludwigshafen; Ruth Müller, Friedelsheim; Hubert Sauter; Herbert Bayer, both of Mannheim; Thomas Grote, Schifferstadt; Andreas Gypser, Mannheim; Reinhard Kirstgen, Neustadt; Bernd Müller, Frankenthal; Arne Ptock, Ludwigshafen; Franz Röhl, Schifferstadt; Gisela Lorenz, Neustadt; Eberhard Ammermann, Heppenheim; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/423,860

(22) PCT Filed: May 15, 1998

(86) PCT No.: PCT/EP98/02880

§ 371 Date: Nov. 17, 1999

§ 102(e) Date: Nov. 17, 1999

(87) PCT Pub. No.: WO98/53682

PCT Pub. Date: Dec. 3, 1998

(30) Foreign Application Priority Data

May 28, 1997 (DE) .............................. 197 22 222

(51) Int. Cl.[7] .............................. A01N 33/24; A01N 35/10
(52) U.S. Cl. .............................................. 514/640
(58) Field of Search .............................. 514/640

(56) References Cited

U.S. PATENT DOCUMENTS 5,977,399 * 11/1999 Muller et al. ...................... 560/29

FOREIGN PATENT DOCUMENTS

2199422 * 8/1995 (CA) .
195 40 989   5/1997 (DE) .
195 45 878   6/1997 (DE) .
195 48 370   7/1997 (DE) .
95/18789    7/1995 (WO) .
95/21153  * 8/1995 (WO) .
95/21154    8/1995 (WO) .
95/21156    8/1995 (WO) .
96/06072    2/1996 (WO) .
96/16026    5/1996 (WO) .
96/16030    5/1996 (WO) .
96/32373   10/1996 (WO) .
97/01530    1/1997 (WO) .
97/02255    1/1997 (WO) .

* cited by examiner

Primary Examiner—Phyllis G. Spivack
(74) Attorney, Agent, or Firm—Keil & Weinkauf

(57) ABSTRACT

A method for control of harmful fungi is provided by treating the fungi, or the materials, plants, the soil or seeds to be protected against fungal infection, with an effective amount of a bisoxime of the formula I

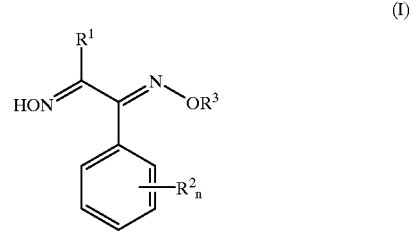

or a salt or adduct thereof, the index and the substituents having the following meanings:

$R^1$ is halogen, alkyl or haloalkyl;

$R^2$ is cyano, nitro, halogen, alkyl, haloalkyl, alkoxy, haloalkoxy, alkylthio, alkylamino, dialkylamino, alkylaminocarbonyl, substituted or unsubstituted phenyl, phenoxy or phenylthio;

n is 0, 1, 2 or 3;

$R^3$ is alkyl, haloalkyl, alkenyl, haloalkenyl, alkynyl, haloalkynyl or phenylalkyl.

16 Claims, No Drawings

METHOD FOR COMBATING HARMFUL FUNGI

This application is a 371 of PCT/EP098/02880 filed May 5, 1998.

The present invention relates to a method of controlling harmful fungi, which comprises treating the fungi, or the materials, plants, the soil or seeds to be protected against fungal infection, with an effective amount of a bisoxime of the formula I

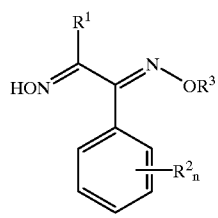

(I)

or a salt or adduct thereof, the index and the substituents having the following meanings:

$R^1$ is halogen, $C_1$–$C_6$-alkyl or $C_1$–$C_4$-haloalkyl;

$R^2$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylaminocarbonyl, phenyl, phenoxy or phenylthio, it being possible for these radicals to be partially or fully halogenated in the phenyl moiety and/or to have attached to them one to three of the following groups: cyano, formyl, $C_1$–$C_4$-alkyl, $C_1$–$C_4$-haloalkyl, $C_1$–$C_4$-alkylcarbonyl, $C_1$–$C_4$-alkoxy, $C_1$–$C_4$-haloalkoxy, phenyl or naphthyl;

n is 0, 1, 2 or 3, it being possible for the radicals $R^2$ to be different if n is 2 or 3;

$R^3$ is $C_1$–$C_{10}$-alkyl, $C_1$–$C_6$-haloalkyl, $C_3$–$C_6$-alkenyl, $C_3$–$C_6$-haloalkenyl, $C_3$–$C_6$-alkynyl, $C_3$–$C_6$-haloalkynyl or phenyl-$C_1$–$C_4$-alkyl.

In addition, the invention relates to the use of the compounds I for the preparation of a composition which is suitable for controlling harmful fungi.

Bisoximes of the formula I defined at the outset have been disclosed in the literature (cf. WO-A 95/18,789; WO-A 95/21,153; WO-A 95/21,154; WO-A 95/21,156; WO-A 96/06,072; WO-A 96/16,026; WO-A 96/16,030; WO-A 97/01,530; WO-A 97/02,255; DE Appl. No. 19 540 989; DE Appl. No. 19 545 878; DE Appl. No. 19 548 370) as intermediates for the preparation of fungicidally active ingredients of the type of the formula A:

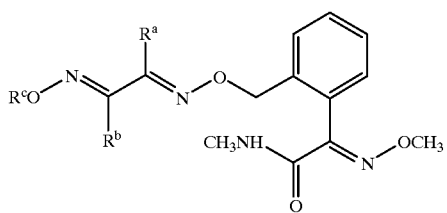

(A)

However, apart from the usefulness of these compounds as intermediates, these documents do not suggest any additional possible applications of the bisoximes.

In addition, PCT/EP 96/01,306 describes processes for the preparation of essentially isomerically pure bisoximes of the type of the compounds I. As regards the use of such compounds, this document refers to the suitability as intermediate for the preparation of the compounds of type (A).

It is an object of the present invention to provide compounds with fungicidal properties.

We have found that this object is achieved by the prior-art bisoximes, which are suitable for controlling harmful fungi in an efficient manner.

The meaning of the collective terms used in the definition of the compounds I can be seen, for example, from the relevant information in WO-A 95/21,156.

As regards their intended use for controlling harmful fungi, particularly suitable compounds I are those where $R^1$ is fluorine, chlorine or bromine (in particular chlorine) or methyl, ethyl, propyl or iso-propyl (in particular methyl or ethyl).

Other preferred compounds I are those where n is 1, 2 or 3 (especially 1 or 2).

In the event that n is 1, preferred compounds I are those where the radical $R^2$ is bonded in the 4-position of the phenyl ring.

In the event that n is 2, preferred compounds I are those where the radicals $R^2$ are bonded in the relative position 2,4 or 3,4 (especially 2,4).

In the event that n is 3, preferred compounds I are those where the radicals $R^2$ are bonded in the relative position 2,4,5 or 2,4,6 (especially 2,4,5).

Especially suitable as radicals $R^2$ are halogen (in particular fluorine, chlorine and bromine), $C_1$–$C_4$-alkyl (in particular methyl), $C_1$–$C_4$-haloalkyl (in particular trifluoromethyl), $C_1$–$C_4$-alkoxy (in particular methoxy), $C_1$–$C_4$-haloalkoxy (in particular trifluoromethoxy) and $C_1$–$C_4$-alkylthio (in particular methylthio), nitro and dimethylamino.

Additional preferred compounds I are those where $R^2$ (preferably one of the radicals $R^2$) is phenyl, phenoxy or phenylthio (in particular phenyl), it being possible for these radicals to have attached to them in the phenyl moiety preferably one to three of the following groups: halogen (in particular chlorine and bromine), $C_1$–$C_4$-alkyl (in particular methyl), $C_1$–$C_4$-haloalkyl (in particular trifluoromethyl), $C_1$–$C_4$-alkoxy (in particular methoxy), and $C_1$–$C_4$-haloalkoxy (in particular trifluoromethoxy).

Other particularly preferred compounds I are those where at least one of the radicals $R^2$ is halogen.

With regard to the radical $R^3$, preferred compounds I are those which have attached to them, in this position, $C_1$–$C_{10}$-alkyl (especially $C_1$–$C_4$-alkyl), $C_3$–$C_6$-alkenyl or $C_3$–$C_6$-haloalkenyl [especially $C_3$–$C_4$-alkenyl which may have attached to it one to three (in particular one or two) halogen atoms (in particular chlorine or bromine)], $C_3$–$C_6$-alkynyl or $C_3$–$C_6$-haloalkynyl [especially $C_3$–$C_4$-alkynyl which may have attached to it one to three (in particular one or two) halogen atoms (in particular chlorine or bromine), or phenyl-$C_1$–$C_4$-alkyl (in particular benzyl).

The compounds I are suitable as fungicides. They are distinguished by outstanding activity against a broad spectrum of phytopathogenic fungi, in particular from the classes of the Ascomycetes, Deuteromycetes, Phycomycetes and Basidiomycetes. Some of them are systemically active, and they can be employed in crop protection as foliar- and soil-acting fungicides.

They are especially important for controlling a large number of fungi on a variety of crop plants, such as wheat, rye, barley, oats, rice, maize, grass, bananas, cotton, soya, coffee, sugarcane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit,

*Botrytis cinerea* (gray mold) on strawberries, vegetables, ornamentals and grapevines,

*Cercospora arachidicola* on peanuts,

*Erysiphe cichoracearum* and *Sphaerotheca fuliginea* on cucurbits,

*Erysiphe graminis* (powdery mildew) on cereals,

Fusarium and Verticillium species on a variety of plants,

Helminthosporium species on cereals,

Mycosphaerella species on bananas,

*Phytophthora infestans* on potatoes and tomatoes,

*Plasmopara viticola* on grapevines,

*Podosphaera leucotricha* on apples,

*Pseudocercosporella herpotrichoides* on wheat and barley,

Pseudoperonospora species on hops and cucumbers,

Puccinia species on cereals,

*Pyricularia oryzae* on rice,

Rhizoctonia species on cotton, rice and turf,

*Septoria nodorum* on wheat,

*Uncinula necator* on grapevines,

Ustilago species on cereals and sugarcane, and

*Venturia inaequalis* (scab) on apples.

The compounds I are particularly suitable for controlling Erysiphe species and *Plasmopara viticola*.

In addition, the compounds I are suitable for controlling harmful fungi such as *Paecilomyces variotii* in the protection of materials (eg. wood, paper, paint dispersions, fibers or fabrics) and in the protection of stored products.

The compounds I are applied by treating the fungi, or the plants, seeds, materials or the soil to be protected against fungal infection, with a fungicidally active amount of the active ingredients. Application may be effected before or after infection of the materials, plants, or seeds by the fungi.

When applied in crop protection, the rates of application are from 0.001 to 5.0 kg, preferably 0.01 to 2 kg, in particular 0.05 to 1 kg, of active ingredient per ha, depending on the nature of the desired effect.

In the treatment of seed, amounts of from 0.001 to 0.1 g, preferably 0.01 to 0.05 g, of active ingredient are generally required per kilogram of seed.

When used in the protection of materials or stored products, the rate of application of active ingredient depends on the nature of the field of application and of the desired effect. Normal rates of application in the protection of materials are, for example, from 0.001 g to 2 kg, preferably 0.005 g to 1 kg, of active ingredient per cubic meter of material treated.

Due to the basic character of the nitrogen atoms, the compounds I may form salts or adducts with acids and metal ions and may be applied in the form of pure compounds and also in the form of salts or adducts of this kind.

Examples of inorganic acids are hydrohalic acids such as hydrogen fluoride, hydrogen chloride, hydrogen bromide and hydrogen iodide, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids with straight-chain or branched alkyl radicals having 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals with 1 to 20 carbon atoms), arylphosphonic acids or -diphosphonic acids (aromatic radicals such as phenyl and naphthyl which have attached to them one or two phosphono radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid and the like.

Metal ions which are suitable are, in particular, the ions of the elements of the first to eighth sub-groups, particularly chromium, manganese, iron, cobalt, nickel, copper, zinc, and also of the second main group, particularly calcium and magnesium, and of the third and fourth main groups, in particular aluminum, tin and lead.

If appropriate, the metals may exist in the various valencies which they may assume.

The compounds I or their salts can be converted into the customary formulations, eg. solutions, emulsions, suspensions, dusts, powders, pastes and granules. The use form depends on the intended purpose; it is intended to ensure in each case a fine and uniform distribution of the compound according to the invention.

The formulations are prepared in a known manner, eg. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as non-ionic and anionic emulsifiers (eg. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol or formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Powders, materials for spreading and dusts can be prepared by mixing or concomitantly grinding the active substances with a solid carrier.

Granules, eg. coated granules, impregnated granules and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, eg. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

The following are examples of formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in-a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% a by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, eg. in the form of directly sprayable solutions, powders, suspensions or dispersions, emulsions, oil dispersions, pastes, dusts, materials for spreading, or granules, by means of spraying, atomizing, dusting, spreading or pouring. The use forms depend entirely on the intended purposes; it is intended to ensure in each case the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such, or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives. Various types of oils, herbicides, fungicides, other pesticides, or bactericides may be added to the active ingredients, if appropriate just immediately prior to use (tank mix). These agents can be admixed with the agents according to the invention in a weight ratio of 1:10 to 10:1.

In the use form as fungicides, the compositions according to the invention can also be present together with other active ingredients, eg. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl)benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane;

amines such as 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, (8-(1,1-dimethylethyl)-N-ethyl-N-propyl-1,4-dioxaspiro[4.5]decane-2-methanamine;

azoles such as 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, 1-[2-(2,4-dichlorophenyl)-pentyl]-1H-1,2,4-triazole, 2,4'-difluoro-a-(1H-1,2,4-triazolyl-1-methyl)-benzhydryl alcohol, 1-((bis-(4-fluorophenyl)methylsilyl)methyl)-1H-1,2,4-triazole, 1-[2RS,4RS;2RS,4SR)-4-bromo-2-(2,4-dichlorophenyl)tetrahydrofuryl]-1H-1,2,4-triazole, 2-(4-chlorophenyl)-3-cyclopropyl-1-(1H-1,2,4-triazol-1-yl)-butan-2-ol, (+)-4-chloro-4-[4-methyl-2-(1H-1,2,4-triazol-1-ylmethyl)-1,3-dioxolan-2-yl]-phenyl 4-chlorophenyl ether, (E)-(R,S)-1-(2,4-dichlorophenyl)-4,4-dimethyl-2-(1H-1,2,4-triazol-1-yl)pent-1-en-3-ol, 4-(4-chlorophenyl)-2-phenyl-2-(1H-1,2,4,-triazolylmethyl)butyronitrile, 3-(2,4-dichlorophenyl)-6-fluoro-2-(1H-1,2,4-triazol-1-yl)quinazolin-4(3H)-one, (R,S)-2-(2,4-dichlorophenyl)-1-H-(1,2,4-triazol-1-yl)-hexano-2-ol, (1RS,5RS;1RS,5SR)-5-(4-chlorobenzyl)-2,2-dimethyl-1-(1H-1,2,4-triazol-1-ylmethyl)cyclopentanol, (R,S)-1-(4-chlorophenyl)-4,4-dimethyl-3-(1H-1,2,4-triazol-1-yl methyl)pentan-3-ol, (+)-2-(2,4,-dichlorophenyl)-3-(1H-1,2,4-triazolyl)propyl 1,1,2,2-tetrafluoroethyl ether, (E)-1-[1-[4-chloro-2-trifluoromethyl)-phenyl]imino)-2-propoxyethyl]-1H-imidazole, 2-(4-chlorophenyl)-2-(1H -1,2,4-triazol-1-ylmethyl) hexanonitrile;

α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]-phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl]acetamide;

anilinopyrimidines such as N-(4,6-dimethylpyrimidin-2-yl)aniline, N-[4-methyl-6-(1-propynyl)pyrimidin-2-yl]aniline, N-[4-methyl-6-cyclopropylpyrimidin-2-yl]aniline;

phenylpyrroles such as 4-(2,2-difluoro-1,3-benzodioxol-4-yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, N-methyl-, N-ethyl-(4-trifluoromethyl,-2-[3',4'-dimethoxyphenyl]benzamide, hexachlorobenzene, methyl N-(2,6-dimethylphenyl)-N-(2-furoyl)-DL-alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl(-5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]acetamide, N-(3-chloro-2,6-dinitro-4-trifluoromethylphenyl)-5-trifluoromethyl-3-chloro-2-aminopyridine.

SYNTHESIS EXAMPLES

With due modification of the starting compounds, the protocols shown in the synthesis examples below were used for obtaining further compounds I. The resulting compounds, together with physical data, are listed in the tables which follow.

1. 1-[4-Chlorophenyl]propane-1,2-dione 2-oxime

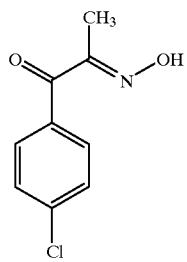

First of all, 100 ml of saturated etheric hydrochloric acid were added dropwise at −10° C. to −20° C. to a solution of 45 g (0.27 mol) of 4-chloropropiophenone and 500 ml of toluene, and then a solution of 44.5 g of n-butylnitrile in 200 ml of diethyl ether were added. After approx. 24 hours at 20–220° C., the reaction mixture was poured into ice-water. The organic phase was isolated and washed three times with 1 N sodium hydroxide solution and once with 3 N sodium hydroxide solution. The sodium hydroxide phases were combined and acidified with 20% strength sulfuric acid to a pH of 5. The precipitate formed during this process was isolated and dissolved in tert-butyl methyl ether. The solution was dried over sodium sulfate, and the solvent was removed under reduced pressure. This gave 81.4 g of the product as a pale yellow solid.

$^1$H NMR (CDCl$_3$, δ in ppm): 2.2 (s, 3H); 7.4 (m, 2H); 7.8 (m,2H); 9.0 (s, 1H)

2. 4-Chlorophenyl-[E/E,Z/E]-2-hydroxyimino-1-methoxyiminopropane

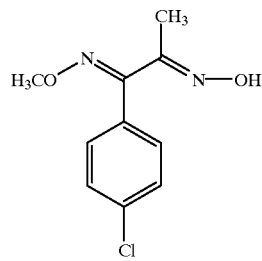

68.5 g (0.82 mol) of O-methylhydroxylamine hydrochloride and 97 g (1.23 mol) of pyridine were added to a mixture of 81.4 g of 1-[4-chlorophenyl]-propane-1,2-dione 2-oxime and 500 ml of methanol. After approx. 24 hours at 22–25° C., the reaction mixture was poured into 10% strength hydrochloric acid. The mixture was extracted repeatedly with tert-butyl methyl ether. The organic phases were combined, washed with water and dried over sodium sulfate. The solvent was subsequently removed under reduced pressure. This gave 89.4 g of the product (isomer mixture).

4-Chlorophenyl-[E/E]-2-hydroxyimino-1-methoxyiminopropane

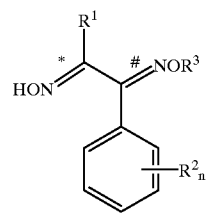

26.6 g (0.2 mol) of aluminum trichloride were slowly added at 40° C. to a solution of 89.4 g (0.39 mol) of 4-chlorophenyl-[E/E,Z/E]-2-hydroxyimino-1-methoxyiminopropane in 500 ml of toluene. After 5 hours at 50° C. and a further 24 hours at 20–22° C., the reaction mixture was poured into a mixture of ice and 10% strength hydrochloric acid. The resulting mixture was extracted repeatedly with tert-butyl methyl ether. The organic phases were combined, washed with 10% strength hydrochloric acid and subsequently with water, and dried. The solvent was subsequently removed under reduced pressure. This gave 50.6 g of the product as a colorless solid (m.p.: 175–178° C.; isomeric ratio 98.5% E/E and 1.5% Z/E).

$^1$H NMR (CDCl$_3$, δ in ppm): 2.1 (s, 3H); 4.0 (s, 3H); 7.1 (m, 2H); 7.3 (m, 2H); 8.0 (s, 1H)

TABLE I (I)

| No. | R$^1$ | R$^2_n$ | R$^3$ | */# | Physical data [m.p. (° C.); IR (cm$^{-1}$); $^1$H NMR (δ in ppm)] |
|---|---|---|---|---|---|
| I.1 | CH$_3$ | — | CH$_3$ | E/E | m.p.: 160–162 |
| I.2 | CH$_3$ | 3-CN | CH$_3$ | E/E | m.p.: 163–166 |
| I.3 | CH$_3$ | 4-CN | CH$_3$ | E/E | m.p.: 165–170 |
| I.4 | CH$_3$ | 4-F | CH$_3$ | E/E | m.p.: 156–157 |
| I.5 | CH$_3$ | 4-F | CH$_2$CH$_3$ | E/E | m.p.: 75–91 |

TABLE I-continued (I)

$$\underset{HON}{\overset{R^1}{\underset{*}{\|}}}\overset{\#}{\underset{}{\|}}NOR^3$$

(with phenyl ring substituted by $R^2_n$)

| No. | $R^1$ | $R^2_n$ | $R^3$ | */# | Physical data [m.p. (°C.); IR (cm$^{-1}$); $^1$H NMR (δ in ppm)] |
|---|---|---|---|---|---|
| I.6 | CH$_3$ | 4-F | CH$_2$CH$_3$ | E/Z | m.p.: 75–91 |
| I.7 | CH$_3$ | 4-F | CH(CH$_3$)$_2$ | E/E | m.p.: 120–130 |
| I.8 | CH$_3$ | 4-F | CH(CH$_3$)$_2$ | E/E + E/Z | m.p.: 77–80 |
| I.9 | CH$_3$ | 4-F | CH(CH$_3$)$_2$ | E/Z | m.p.: 74–77 |
| I.10 | CH$_3$ | 4-F | C(CH$_3$)$_3$ | E/E | m.p.: 96–130 |
| I.11 | CH$_3$ | 4-F | (CH$_2$)$_3$CH$_3$ | E/E | m.p.: 98–100 |
| I.12 | CH$_3$ | 4-F | (CH$_2$)$_3$CH$_3$ | E/Z | IR: 1606, 1510, 1234, 1028 |
| I.13 | CH$_3$ | 4-F | (CH$_2$)$_4$CH$_3$ | E/Z | IR: 1606, 1510, 1234, 1014 |
| I.14 | CH$_3$ | 4-F | (CH$_2$)$_5$CH$_3$ | E/E | m.p.: 66–74 |
| I.15 | CH$_3$ | 4-F | CH$_2$—CH=CH$_2$ | E/E + E/Z | m.p.: 95–105 |
| I.16 | CH$_3$ | 4-F | CH$_2$C≡CH | E/E | m.p.: 149–150 |
| I.17 | CH$_3$ | 4-F | CH$_2$—C$_6$H$_5$ | E/E + E/Z | m.p.: 155–161 |
| I.18 | CH$_3$ | 3-Cl | CH$_3$ | E/E | m.p.: 151–152 |
| I.19 | CH$_3$ | 4-Cl | CH$_3$ | E/E | m.p.: 174–176 |
| I.20 | CH$_3$ | 4-Cl | CH$_3$ | E/E + E/Z | m.p.: 103–103 [sic] |
| I.21 | CH$_3$ | 4-Cl | CH$_2$CH$_3$ | E/E | m.p.: 103–105 |
| I.22 | CH$_3$ | 4-Cl | CH$_2$CH$_2$CH$_3$ | E/Z | m.p.: 81–84 |
| I.23 | CH$_3$ | 4-Cl | CH(CH$_3$)$_2$ | E/E | m.p.: 124–126 |
| I.24 | CH$_3$ | 4-Cl | (CH$_2$)$_3$CH$_3$ | E/Z | m.p.: 47–50 |
| I.25 | CH$_3$ | 4-Cl | C(CH$_3$)$_3$ | E/E | m.p.: 132–135 |
| I.26 | CH$_3$ | 4-Cl | (CH$_2$)$_5$CH$_3$ | E/E | m.p.: 43–45 |
| I.27 | CH$_3$ | 4-Cl | CH$_2$C≡CH | E/E + E/Z | m.p.: 108–111 |
| I.28 | CH$_3$ | 4-Cl | CH$_2$C≡CH | E/E | m.p.: 149–154 |
| I.29 | CH$_3$ | 4-Cl | CH$_2$—C$_6$H$_5$ | E/E | m.p.: 113–116 |
| I.30 | CH$_2$CH$_3$ | 4-Cl | CH$_3$ | E/E | m.p.: 159–161 |
| I.31 | CH$_2$CH$_3$ | 4-Cl | CH$_2$CH$_2$CH$_3$ | E/Z | IR: 1492, 1093, 992, 940 |
| I.32 | CH$_2$CH$_3$ | 4-Cl | CH(CH$_3$)$_2$ | E/E | m.p.: 144 |
| I.33 | CH$_2$CH$_3$ | 4-Cl | (CH$_2$)$_3$CH$_3$ | E/E | m.p.: 79–82 |
| I.34 | CH$_2$CH$_3$ | 4-Cl | (CH$_2$)$_3$CH$_3$ | E/Z | IR: 1492, 1093, 1014, 834 |
| I.35 | CH$_2$CH$_3$ | 4-Cl | CH$_2$C≡CH | E/E | m.p.: 106–109 |
| I.36 | CH$_3$ | 4-Br | CH$_3$ | E/E | m.p.: 175–178 |
| I.37 | CH$_3$ | 4-Br | CH$_3$ | E/E + E/Z | m.p.: 98–103 |
| I.38 | CH$_3$ | 4-Br | CH$_2$CH$_3$ | E/Z | m.p.: 100–102 |
| I.39 | CH$_3$ | 4-Br | (CH$_2$)$_3$CH$_2$ | E/E | m.p.: 49–52 |
| I.40 | CH$_3$ | 4-Br | (CH$_2$)$_5$CH$_2$ | E/Z | m.p.: 50–53 |
| I.41 | CH$_3$ | 4-Br | CH$_2$C≡CH | E/E | m.p.: 119–120 |
| I.42 | CH$_3$ | 4-CH$_3$ | CH$_3$ | E/E | m.p.: 152–155 |
| I.43 | CH$_3$ | 4-CH(CH$_3$)$_2$ | CH$_3$ | E/E | m.p.: 182–183 |
| I.44 | CH$_3$ | 4-CH(CH$_3$)$_2$ | CH$_2$C≡CH | E/E | NMR: 2.1(s, 3H); 2.95(m, 1H); 4.7(m, 2H) |
| I.45 | CH$_3$ | 4-C(CH$_3$)$_3$ | CH$_3$ | E/Z | m.p.: 183–188 |
| I.46 | CH$_3$ | 4-C(CH$_3$)$_3$ | CH$_3$ | E/E | m.p.: 190–192 |
| I.47 | CH$_3$ | 4-C(CH$_3$)$_3$ | CH$_3$ | E/E + E/Z | m.p.: 78–81 |
| I.48 | CH$_3$ | 4-C(CH$_3$)$_3$ | CH$_2$CH$_3$ | E/E | m.p.: 79–82 |
| I.49 | CH$_3$ | 4-C(CH$_3$)$_3$ | (CH$_2$)$_3$CH$_3$ | E/E | IR: 1634, 1017, 1001, 975 |
| I.50 | CH$_3$ | 4-C(CH$_3$)$_3$ | (CH$_2$)$_5$CH$_3$ | E/Z | IR: 1462, 1364, 1017, 996 |
| I.51 | CH$_3$ | 4-C(CH$_3$)$_3$ | CH$_2$—C$_6$H$_5$ | E/E + E/Z | m.p.: 185–194 |
| I.52 | CH$_3$ | 4-C(CH$_3$)$_3$ | CH$_3$ | E/Z | IR: 1462, 1263, 1057, 1034 |
| I.53 | CH$_3$ | 2-CF$_3$ | CH$_2$CH$_3$ | E/E | m.p.: 116–118 |
| I.54 | CH$_3$ | 3-CF$_3$ | CH$_3$ | E/E | m.p.: 163–165 |
| I.55 | CH$_3$ | 3-CF$_3$ | CH$_3$ | E/Z | IR: 1338, 1299, 1183, 1117 |
| I.56 | CH$_3$ | 3-CF$_3$ | CH$_2$CH$_3$ | E/E | m.p.: 120–122 |
| I.57 | CH$_3$ | 3-CF$_3$ | CH$_2$CH$_3$ | E/Z | m.p.: 49–51 |
| I.58 | CH$_3$ | 3-CF$_3$ | (CH$_2$)$_3$CH$_3$ | E/E + E/Z | IR: 1327, 1177, 1167, 1123 |
| I.59 | CH$_3$ | 3-CF$_3$ | CH$_2$—C$_6$H$_5$ | E/E | m.p.: 117–120 |
| I.60 | CH$_3$ | 3-CF$_3$ | CH$_2$—C$_6$H$_5$ | E/Z | m.p.: 70–72 |
| I.61 | CH$_3$ | 4-CF$_3$ | CH$_3$ | E/E | m.p.: 198–201 |
| I.62 | CH$_3$ | 4-CF$_3$ | CH$_3$ | E/Z + E/E | IR: 1608, 1066, 1011, 998 |
| I.63 | CH$_3$ | 4-CF$_3$ | CH$_2$CH$_3$ | E/E | m.p.: 171–174 |
| I.64 | CH$_3$ | 4-CF$_3$ | CH$_2$CH$_3$ | E/Z | m.p.: 58–61 |
| I.65 | CH$_3$ | 4-CF$_3$ | (CH$_2$)$_3$CH$_3$ | E/E | m.p.: 118–124 |
| I.66 | CH$_3$ | 4-CF$_3$ | (CH$_2$)$_3$CH$_3$ | E/Z | IR: 1326, 1168, 1139, 1070 |
| I.67 | CH$_3$ | 4-CF$_3$ | (CH$_2$)$_5$CH$_3$ | E/E | m.p.: 108–111 |
| I.68 | CH$_3$ | 4-CF$_3$ | (CH$_2$)$_5$CH$_3$ | E/Z | IR: 1325, 1168, 1129, 1070 |

TABLE I-continued

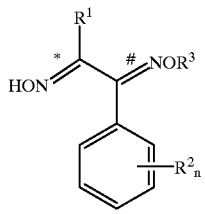

(I)

| No. | $R^1$ | $R^2_n$ | $R^3$ | */# | Physical data [m.p. (° C.); IR (cm$^{-1}$); $^1$H NMR (δ in ppm)] |
|---|---|---|---|---|---|
| I.69 | $CH_3$ | 4-$CF_3$ | $CH_2$—$C_6H_5$ | E/E + E/Z | m.p.: 150–153 |
| I.70 | $CH_3$ | 4-$CF_3$ | $CH_2C\equiv CH$ | E/E | m.p.: 145–150 |
| I.71 | $CH_3$ | 4-$OCH_3$ | $CH_3$ | E/Z | m.p.: 93–95 |
| I.72 | $CH_3$ | 4-$OCH_3$ | $CH_2CH_3$ | E/Z | m.p.: 71–74 |
| I.73 | $CH_3$ | 4-$OCH_3$ | $(CH_2)_3CH_3$ | E/Z | IR: 1517, 1252, 1175, 1030 |
| I.74 | $CH_3$ | 4-$OCH_3$ | $(CH_2)_5CH_3$ | E/E | IR: 1512, 1251, 1175, 993 |
| I.75 | $CH_3$ | 4-$OCH_3$ | $CH_2$—$C_6H_5$ | E/Z | m.p.: 94–96 |
| I.76 | $CH_3$ | 2,4-$Cl_2$ | $CH_3$ | E/E | m.p.: 124–126 |
| I.77 | $CH_3$ | 2,4-$Cl_2$ | $CH_2CH_3$ | E/E | m.p.: 90–93 |
| I.78 | $CH_3$ | 2,4-$Cl_2$ | $(CH_2)_3CH_3$ | E/E | m.p.: 62–66 |
| I.79 | $CH_3$ | 2,4-$Cl_2$ | $(CH_2)_5CH_3$ | E/E | m.p.: 80–84 |
| I.80 | $CH_3$ | 2,4-$Cl_2$ | $CH_2$—$C_6H_5$ | E/E | m.p.: 136–139 |
| I.81 | $CH_3$ | 2-F, 4-$CF_3$ | $CH_3$ | E/E | NMR: 2.2(s, 3H); 4.0(s, 3H) |
| I.82 | $CH_3$ | 2-F, 4-$CF_3$ | $CH_2CH_3$ | E/E | IR: 1425, 1330, 1133, 1048, 907 |
| I.83 | $CH_3$ | 2-F, 4-$CF_3$ | $(CH_2)_3CH_3$ | E/Z + E/E | IR: 1428, 1331, 1176, 1133 |
| I.84 | $CH_3$ | 2-F, 4-$CF_3$ | $(CH_2)_5CH_3$ | E/E | IR: 1424, 1332, 1148, 988 |
| I.85 | $CH_3$ | 2-F, 4-$CF_3$ | $(CH_2)_5CH_3$ | E/Z + E/E | IR: 1426, 1329, 1173, 1135 |
| I.86 | $CH_3$ | 2-F, 4-$CF_3$ | $CH_2$—$C_6H_5$ | E/E | m.p.: 138 |
| I.87 | $CH_3$ | 3-$NO_2$ | $CH_3$ | E/E | m.p.: 149–157 |
| I.88 | $CH_3$ | 3-$NO_2$ | $CH_2CH_3$ | E/E | m.p.: 147 |
| I.89 | $CH_3$ | 4-$N(CH_3)_2$ | $CH_3$ | E/Z | m.p.: 132–136 |
| I.90 | $CH_3$ | 4-NH—$COCH_2CH_3$ | $CH_3$ | E/E | m.p.: 210 |
| I.91 | $CH_3$ | 4-NH—$COCH_2CH_3$ | $CH_3$ | E/Z | m.p.: 190 |
| I.92 | $CH_3$ | 4-$NO_2$ | $CH_3$ | E/E | m.p.: 154–155 |
| I.93 | $CH_3$ | 4-$C_6H_5$ | $CH_3$ | E/E | m.p.: 178–182 |
| I.94 | $CH_3$ | 4-[4-F—$C_6H_4$] | $CH_3$ | E/E | m.p.: 208–210 |
| I.95 | $CH_3$ | 4-[4-Cl—$C_6H_4$] | $CH_3$ | E/E | m.p.: 192–205 |
| I.96 | $CH_3$ | 4-[4-$CF_3$—$C_6H_4$] | $CH_3$ | E/E | m.p.: 205–208 |
| I.97 | $CH_3$ | 4-[4-CHO—$C_6H_4$] | $CH_3$ | E/E | m.p.: 165–175 |
| I.98 | $CH_3$ | 4-[4-$COCH_3$—$C_6H_4$] | $CH_3$ | E/E | m.p.: 145–150 |
| I.99 | $CH_3$ | 4-[2-F, 4-$CH_3$—$C_6H_3$] | $CH_3$ | E/E | m.p.: 170–176 |
| I.100 | $CH_3$ | 4-[4-$CH(CH_3)_2$—$C_6H_4$] | $CH_3$ | E/E | m.p.: 186–188 |
| I.101 | $CH_3$ | 4-[3,5-$(CF_3)_2$—$C_6H_3$] | $CH_3$ | E/E | m.p.: 209–211 |
| I.102 | $CH_3$ | 4-[3,5-$Cl_2$—$C_6H_3$] | $CH_3$ | E/E | m.p.: 185–188 |
| I.103 | $CH_3$ | 4-[2-$OCH_3$—$C_6H_4$] | $CH_3$ | E/E | m.p.: 168 |
| I.104 | $CH_3$ | 4-[4-$CH_3$—$C_6H_4$] | $CH_3$ | E/E | m.p.: 162–174 |
| I.105 | $CH_3$ | 4-[2-naphthyl-$C_6H_4$] | $CH_3$ | E/E | m.p.: 218–225 |

Examples of the action-against harmful fungi:

The fungicidal action of the compounds of the formula I was demonstrated by the following experiments:

The active ingredients were formulated as a 10% emulsion in a mixture of 63% by weight of cyclohexanone and 27% by weight of emulsifier and diluted with water to give the desired concentration.

1. Action against *Erysiphe graminis* var. *tritiei* (powdery mildew of wheat)

Leaves of wheat seedlings (cultivar "Frühgold") were first of all treated with the aqueous formulation of the active ingredients (rate of application: 250 ppm). After approx. 24 hours, the plants were dusted with spores of powdery mildew wheat (*Erysiphe graminis* var. *tritici*). The plants thus treated were subsequently incubated for 7 days at 20–22° C. and a relative atmospheric humidity of 75–80%. The extent of fungal development was subsequently determined.

In this test, the plants which had been treated with the compounds I.5, I.15, I.19, I.20, I.21, I.22, I.27, I.28, I.36, I.42, I.63 and I.76 showed a disease level of 10% or less, while the disease level of the untreated (control) plants was 75%.

2. Action against *Plasmopara viticola*

Leaves of grapevines in pots, cultivar "Müller-Thurgau", were sprayed to run-off point with an aqueous formulation of active ingredient. To assess the long-term action of the substances, the plants were placed in the greenhouse for 7 days after the spray coating had dried on. Only then were the leaves inoculated with an aqueous zoospore suspension of *Plasmopara viticola*. Thereafter, the grapevines were placed first of all in a water-vapor-saturated chamber for 48 hours at 24° C. and subsequently in the greenhouse for 5 days at from 20 to 30° C. After this time, the plants were returned into a humid chamber for 16 hours to accelerate the eruption of sporangiophores. The extent to which the disease had developed on the undersides of the leaves was then determined visually.

In this test, the plants which had been treated with 250 ppm of the compounds I.39, I.44 and I.83 showed a disease level of 15% or less, while the disease level of the untreated (control) plants was 70%.

We claim:

1. A method of controlling harmful fungi, which comprises treating the fungi, or the materials, plants, the soil or seeds to be protected against fungal infection, with an effective amount of a bisoxime of the formula I

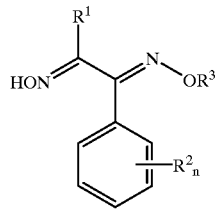

or a salt or adduct thereof, wherein $R^1$ is halogen, $C_1$–$C_6$-alkyl or $C_1$–$C_4$-haloalkyl;

$R^2$ is cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylaminocarbonyl, phenyl, phenoxy or phenylthio, wherein the phenyl moiety is unsubstituted or partially or fully halogenated, or the phenyl moiety carries one, two or three substituents selected from the following groups: cyano, formyl, $C_1$–$C_4$-alkyl, $C_1$–$C_4$-haloalkyl, $C_1$–$C_4$-alkylcarbonyl, $C_1$–$C_4$-alkoxy, $C_1$–$C_4$-haloalkoxy, phenyl and naphthyl, in which case a non-substituted carbon ring member of the phenyl moiety carries a hydrogen atom or a halogen atom;

n is 0, 1, 2 or 3, and the radicals $R^2$ are identical or different when n is 2 or 3;

$R^3$ is $C_1$–$C_{10}$-alkyl, $C_1$–$C_6$-haloalkyl, $C_3$–$C_6$-alkenyl, $C_3$–$C_6$-haloalkenyl, $C_3$–$C_6$-alkynyl, $C_3$–$C_6$-haloalkynyl or phenyl-$C_1$–$C_4$-alkyl.

2. The method of claim 1, wherein $R^1$ is chloride, methyl, trifluoromethyl or ethyl.

3. The method of claim 1, wherein n is different from 0 and at least one of the radicals $R^2$ is halogen.

4. The method of claim 1 wherein crop plants or their environment is treated with from 0.001 to 5.0 kg/ha of the bisoxime I.

5. The method of claim 1 wherein seeds, materials or areas are treated with from 0.01 to 20 g/m³ of the bisoxime I.

6. The method of claim 1, wherein n is 1 and $R^2$ is bonded in the 4-position of the phenyl ring, or n is 2 and the radicals $R^2$ are bonded in the 2,4-position or the 3,4-position of the phenyl ring, or n is 3 and the radicals $R^2$ are bonded in the 2,4,5-position of the 2,4,6-position of the phenyl ring.

7. The method of claim 6, wherein at least one of the radicals $R^2$ is halogen.

8. The method of claim 1, wherein n is 1 and $R^2$ is bonded in the 4-position of the phenyl ring.

9. The method of claim 1, wherein n is 2 and the radicals $R^2$ are bonded in the 2,4-position or the 3,4-position of the phenyl ring.

10. The method of claim 1, wherein n is 2 and the radicals $R^2$ are bonded in the 2,4-position of the phenyl ring.

11. The method of claim 1, wherein $R^2$ is selected from the group consisting of halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, nitro and dimethylamino.

12. The method of claim 11, wherein n is 1 and $R^2$ is bonded in the 4-position of the phenyl ring, or n is 2 and the radicals $R^2$ are bonded in the 2,4-position or the 3,4-position of the phenyl ring, or n is 3 and the radicals $R^2$ are bonded in the 2,4,5-position of the 2,4,6-position of the phenyl ring.

13. The method of claim 12, wherein at least one of the radicals $R^2$ is halogen.

14. The method of claim 1, wherein $R^2$ is selected from the group consisting of fluoride, chloride, bromide, methyl, trifluoromethyl, methoxy, trifluoromethoxy, methylthio, nitro and dimethylamino.

15. The method of claim 1, wherein $R^3$ is $C_1$–$C_{10}$-alkyl, $C_3$–$C_6$-alkenyl, $C_3$–$C_6$-haloalkenyl, $C_3$–$C_6$-alkynyl, $C_3$–$C_6$-haloalkynyl or phenyl-$C_1$–$C_4$-alkyl.

16. The method of claim 1, wherein $R^3$ is $C_1$–$C_4$-alkyl, $C_3$–$C_4$-alkenyl which is unsubstituted or carries one, two or three halogen atoms, $C_3$–$C_4$-alkynyl which is unsubstituted or carries one, two or three halogen atoms, or is benzyl.

* * * * *

UNITED STATES PATENT AND TRADEMARK OFFICE
CERTIFICATE OF CORRECTION

PATENT NO. : 6,255,352 B1
DATED : July 3, 2001
INVENTOR(S) : Grammenos et al.

It is certified that error appears in the above-identified patent and that said Letters Patent is hereby corrected as shown below:

<u>Column 15, claim 4,</u>
Line 42, "is" should be -- are --.

<u>Column 16, claim 6,</u>
Line 8, "of", both instances, should be -- or --.

<u>Column 16, claim 12,</u>
Line 28, "of", both instances, should be -- or --.

<u>Column 16, claim 14,</u>
Line 31, "bromide" should be -- bromine --.

Signed and Sealed this

Fifteenth Day of January, 2002

*Attest:*

JAMES E. ROGAN
*Attesting Officer*   *Director of the United States Patent and Trademark Office*